US006072881A

United States Patent [19]

Linder

[11] Patent Number: 6,072,881

[45] Date of Patent: Jun. 6, 2000

[54] MICROPHONE NOISE REJECTION SYSTEM

[75] Inventor: Frank X. Linder, Oxford, Conn.

[73] Assignee: Chiefs Voice Incorporated, Ridgefield, Conn.

[21] Appl. No.: 08/871,116

[22] Filed: Jun. 9, 1997

Related U.S. Application Data

[60] Provisional application No. 60/015,861, Jul. 8, 1996.

[51] Int. Cl.[7] .............................. A61F 11/06; H03B 29/00

[52] U.S. Cl. .......................................... 381/94.1; 381/94.7

[58] Field of Search ................................ 381/94.1, 94.7, 381/92, 71.1, 56, 57, 71.2, 71.7, 71.8, 71.9

[56] References Cited

U.S. PATENT DOCUMENTS

| | | | |
|---|---|---|---|
| 3,794,766 | 2/1974 | Cox | 381/94.7 |
| 4,153,815 | 5/1979 | Chaplin et al. . | |
| 4,604,501 | 8/1986 | Richmond et al. . | |
| 4,672,674 | 6/1987 | Clough | 381/94.7 |
| 4,736,432 | 4/1988 | Cantrell . | |
| 4,878,188 | 10/1989 | Ziegler, Jr. . | |
| 4,901,354 | 2/1990 | Gollmar et al. . | |
| 4,932,063 | 6/1990 | Nakamura . | |
| 5,033,082 | 7/1991 | Eriksson et al. . | |
| 5,046,103 | 9/1991 | Warnaka et al. . | |
| 5,054,078 | 10/1991 | Schorman et al. . | |
| 5,117,461 | 5/1992 | Moseley . | |
| 5,138,664 | 8/1992 | Kimura et al. . | |
| 5,204,909 | 4/1993 | Cowan . | |
| 5,212,764 | 5/1993 | Ariyoshi | 381/94.7 |
| 5,245,552 | 9/1993 | Andersson | 381/71.2 |
| 5,251,263 | 10/1993 | Andrea et al. . | |
| 5,381,473 | 1/1995 | Andrea et al. . | |
| 5,398,286 | 3/1995 | Balestri et al. . | |
| 5,455,779 | 10/1995 | Sato et al. . | |
| 5,473,701 | 12/1995 | Cezanne | 381/94.7 |
| 5,610,991 | 3/1997 | Janse | 381/94.7 |

*Primary Examiner*—Minsun Oh Harvey
*Attorney, Agent, or Firm*—McCormick, Paulding & Huber LLP

[57] ABSTRACT

An apparatus and method removes repetitive background noise from an information signal originating from a first source, such as a microphone. The noise originates from a second source, such as a siren, and is picked up by the first source along with the information. The noise signal has a characteristic frequency and associated period. The information signal is delayed for a selected period of time based on the characteristic frequency of the repetitive noise signal and forms a phase-shifted or delayed information signal. The delayed information signal is processed with a substantially non-delayed information signal and forms a processed information signal in which the information component is substantial and the noise component is negligible.

26 Claims, 3 Drawing Sheets

MICROPHONE NOISE REJECTION SYSTEM

This application claims the benefit of U.S. Provisional Application Ser. No. 60/015,861, filed Jul. 8, 1996.

The present invention relates to noise rejection systems, and more particularly to a system for rejecting repetitive noise from an information signal.

BACKGROUND OF THE INVENTION

Communication systems are often subject to repetitive background noise. For example, automobile muffler systems, machines on a production floor, engines in a vehicle, boat and airplane, or any other source of repetitive noise can interfere with an acoustic or other pick-up, such as a microphone, hand set of a telephone, hydrophone, vibration sensor, or electronic transducer located near the noise source. In particular, microphones in emergency vehicle communication systems associated with police cars, fire trucks and ambulances pick-up not only a user's voice, but also a repetitive background noise generated by the emergency vehicle siren. This repetitive background noise can often overpower a user's voice so that a user's message is difficult to understand. If voice-activated communication systems are employed, background noise increases the difficulty in recognizing voice commands for automatically turning on and off the communication system.

Microphone noise rejection systems have been developed to minimize the level of background noise relative to the level of the desired information or voice signal. Such noise rejection systems typically comprise dual microphones in which a first microphone primarily receives background noise and a second microphone primarily receives both background noise and an information or voice signal. The noise signal is then added to or subtracted from the information signal in order to cancel noise from the information signal. For example, U.S. Pat. No. 5,381,473 issued to Andrea shows a noise-rejection system that uses two microphones to generate respectively a noise signal and a source signal. The noise and source signals are supplied to a differential amplifier to cancel noise from the source signal. The phases of the noise and source signals must be tightly controlled relative to each other in order to successfully remove unwanted noise from the source signal. Unfortunately, this tight phase control is difficult to achieve because the phases of the noise and source signals are extremely sensitive to slight variation in the length of each signal path from the signal source to the noise rejection processing circuitry. The present invention overcomes the phase control problem by an apparatus and method which is independent of the path length of the signals from the signal source to the noise rejection circuitry.

It is therefore an object of the present invention to substantially eliminate repetitive background noise from an information or voice signal without the disadvantages inherent in the prior approaches to noise rejection.

SUMMARY OF THE INVENTION

The present invention resides in a method of rejecting repetitive noise. A characteristic frequency and associated period of a repetitive noise signal is identified from a first source. An information signal having an information component and a repetitive noise component is received from a second source that is distinct from the first source. The information signal is delayed for a selected period of time based on the characteristic frequency of the repetitive noise signal to form a phase-shifted or delayed information signal. The delayed information signal is processed with a non-delayed information signal to form a processed information signal in which the information component is substantial and the noise component is negligible.

The present invention also resides in an apparatus for removing repetitive background noise. The noise rejection apparatus comprises a first input interface for receiving a repetitive noise signal that has a characteristic frequency and associated period. A second input interface distinct from the first input interface is provided for receiving an information signal having an information component and a repetitive noise component. A means for delaying the information signal for a selected period of time based on the characteristic frequency of the repetitive noise signal forms a phase-shifted or delayed information signal. A means for processing the delayed information signal with a non-delayed information signal is provided to form a processed information signal in which the information component is substantial and the noise component is negligible.

One advantage of the present invention is that the noise rejection system does not suffer from the phase alignment problems inherent in adding or subtracting information and noise signals in order to remove the noise component from the information signal.

Other objects and advantages of the present invention will become apparent in view of the following detailed description and accompanying drawings.

DETAILED DESCRIPTION OF THE PREFERRED EMBODIMENTS

Figure 1:
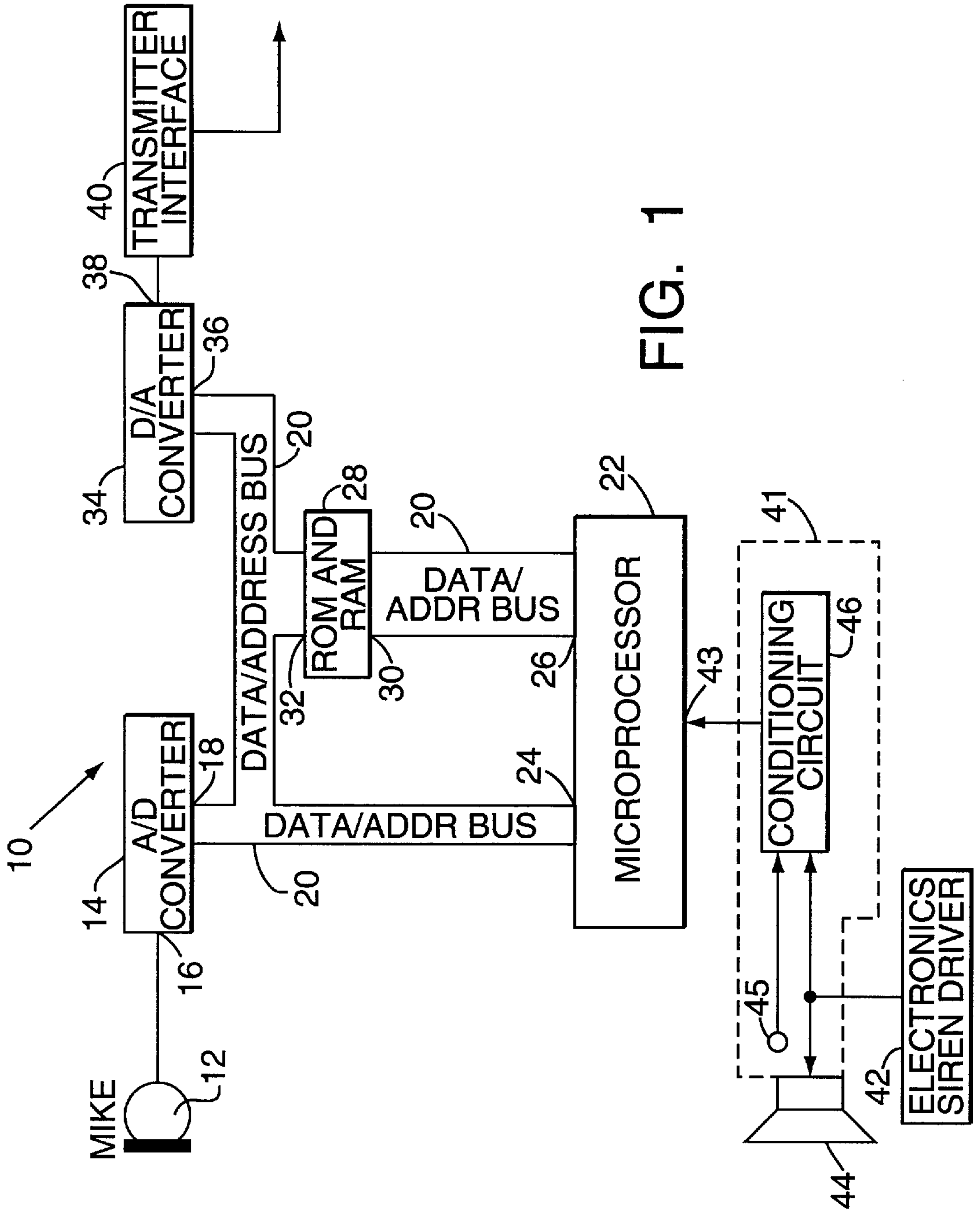
FIG. 1 illustrates in block diagram form a digital embodiment of the microphone noise rejection system in accordance with the present invention.

FIG. 1 schematically illustrates a digital implementation of a noise rejection system 10 for substantially eliminating repetitive background noise from a microphone communication system. The noise rejection system 10 comprises an information signal interface, such as a first microphone 12, for receiving an analog information or voice signal. The first microphone 12 is coupled to an analog-to-digital converter (A/D converter) 14 at an input 16. The A/D converter has a data output at 18 that is coupled via a data/address bus 20 to a processor, such as microprocessor 22, having a data input at 24. The microprocessor 22 has a bus interface at 26 that is coupled to an external memory module 28 at a bus interface at 30. The memory module 28 may include read only memory (ROM) and random access memory (RAM) for aiding the microprocessor 22 in storing and processing digital information. Alternatively, the external memory module 28 may be substituted by internal memory within the microprocessor 22. The memory module 28 has a bus interface at 32 that is coupled via the bus 20 to a D/A converter 34 at a data input 36. The D/A converter 34 includes a data output 38 that is coupled to a transmitter interface 40. The A/D converter 14 and the D/A converter 34 may alternatively be accessed as a decoded address in conjunction with single enable/disable lines.

The noise rejection system further includes an input interface 41 (shown in dashed lines) or means for identifying the characteristic frequency of one or more noise sources. The input interface may be embodied by any combination of standard components which cooperate to identify the characteristic frequency of a noise source. An example of an input interface 41 (as shown in the embodiment of FIG. 1) includes means for sensing the characteristic frequency when the characteristic frequency varies with time. Specifically, the input interface 41 includes a second microphone 45 for receiving an audible siren signal which is emitted by a repetitive noise generator such as siren or loudspeaker 44 that is driven by a siren driver 42. The second microphone 45 must be located at a sufficient distance from the first microphone 12 so that any voice signal pick-up by the second microphone 45 is negligible. Furthermore, the second microphone 45 may be located at the noise source or at a remote location therefrom so long as the second microphone is close enough to the noise source in order to pick up for identification the characteristic frequency of the noise signal.

The input interface 41 further includes a conditioning circuit 46 having inputs coupled to the siren driver 42 and the second microphone 45, and an output coupled to the microprocessor 22 for "cleaning-up" the digital siren signal received directly from the siren driver 42 or an analog siren signal received from the second microphone 45. The conditioning circuit 46 may include or be associated with a switch controlled either manually or by the microprocessor 22 for selecting either the analog siren signal received from the second microphone 45 or the digital siren signal received directly from the siren driver 42. An A/D converter may be provided in association with the second microphone 45 or the conditioning circuit 46 for converting the analog noise signal received by the second microphone 45 before further processing by the microprocessor 22.

Preferably, the siren signal is in the form of a square wave. The characteristic frequency may be selected to be the fundamental frequency or a harmonic of the siren signal. Further, the siren signal may have a characteristic frequency that exhibits a periodicity. For example, the siren frequency may slowly increase and decrease in a recurring manner.

The operation of the digital implementation of the noise rejection system 10 will now be explained in detail. The microphone 12 receives an audio information signal having an information component, such as a user's voice signal, and a repetitive noise component originating from the siren driver 42 via the loudspeaker 44. The microphone 12 continuously generates an analog electrical information signal which is input to the A/D converter 14 at 16. The A/D converter transforms the analog information signal into digital form. The microprocessor 22 processes the digital information after accessing the D/A converter and retrieving the digital information signal via the bus 20.

Simultaneously with the processing of the information signal, the microprocessor 22 directly receives from the input interface 41 a digital repetitive noise signal via the conditioning circuit 46 which "cleans-up" the digital noise signal for digital processing by the microprocessor 22. The microprocessor 22 determines the period associated with the current characteristic frequency of the digital noise signal for purposes to be explained shortly. The microprocessor may also be employed to effect bandwidth spectrum balance, alter intensity ratios among the received signals and improve intelligibility of the signals or any other desired signal characteristics.

The digital information signal retrieved by the microprocessor 22 is then stored either in memory within the microprocessor 22, or within the external memory module 28 for a predetermined delay time that is a function of the period associated with the current characteristic frequency of the digital noise signal received by the microprocessor at input 43. The delay time may range from a portion to a few periods associated with the characteristic frequency of the repetitive noise signal, and preferably corresponds to one full period of the noise signal. The characteristic frequency, as mentioned above, may slowly change over time but may be treated generally as a constant within the brief delay times associated with a few periods of the noise signal.

A digital information signal is stored or delayed in the memory module 28 which acts as a first-in-first-out (FIFO) device. After the delay time elapses, the microprocessor 22 accesses the memory module 28 and retrieves the delayed digital information signal via the data/address bus 20. The microprocessor 22 then digitally subtracts the level of the delayed information signal from that of a non-delayed or current information signal to form a processed information signal in which the level of the information component is substantial and the level of the noise component is negligible. Alternatively, the microprocessor 22 may digitally subtract the level of the non-delayed or current information signal from that of the delayed information signal to form the processed information signal. The effect of the above processing is to cancel the repetitive portion (noise component) of the information signal while substantially maintaining the non-repetitive component (information or voice signals) received by the microphone 12.

Alternatively, the predetermined delay time may correspond to an odd number of half periods of the repetitive noise signal, and preferably corresponds to one half period of the noise signal. In this instance, after the delay time elapses, the microprocessor 22 accesses the memory module 28 and retrieves the delayed digital information signal via the data/address bus 20. The microprocessor 22 then digitally adds the level of the delayed information signal to that of the non-delayed or current information signal to form the processed information signal. The effect of the above processing similarly results in the cancellation of the repetitive portion (noise component) of the information signal while substantially maintaining the non-repetitive component (information or voice signals) received by the microphone 12.

Another embodiment of the input interface or identifying means may include a means for loading and supplying a predetermined characteristic frequency (not shown) to the microprocessor 22 when the characteristic frequency is at a constant and known value. Because the characteristic frequency is predetermined, there is no need for sensing circuitry such as the second microphone 45 shown in FIG. 1.

The noise rejection system of the present invention improves upon the phase alignment difficulties inherent in noise rejection systems which add or subtract information signals with noise signals. With prior noise rejection systems that mathematically manipulate a noise signal with an information signal, it is difficult to establish a reference by which to precisely control the phase relationship between the signals. The present invention, on the other hand, avoids this prior problem by establishing the information signal with the noise as a "reference" among the mathematically manipulated signals. In the present invention as described above, the noise signal is not mathematically manipulated with an information signal. Rather, the noise signal determines the precise delay or phase shift to apply to the information signal for forming a delayed signal relative to the "reference" or current information signal. Once the phase shift is determined, the precisely delayed information signal can be mathematically manipulated with the "reference" or non-delayed information signal in order to cancel noise therefrom.

Figure 2:
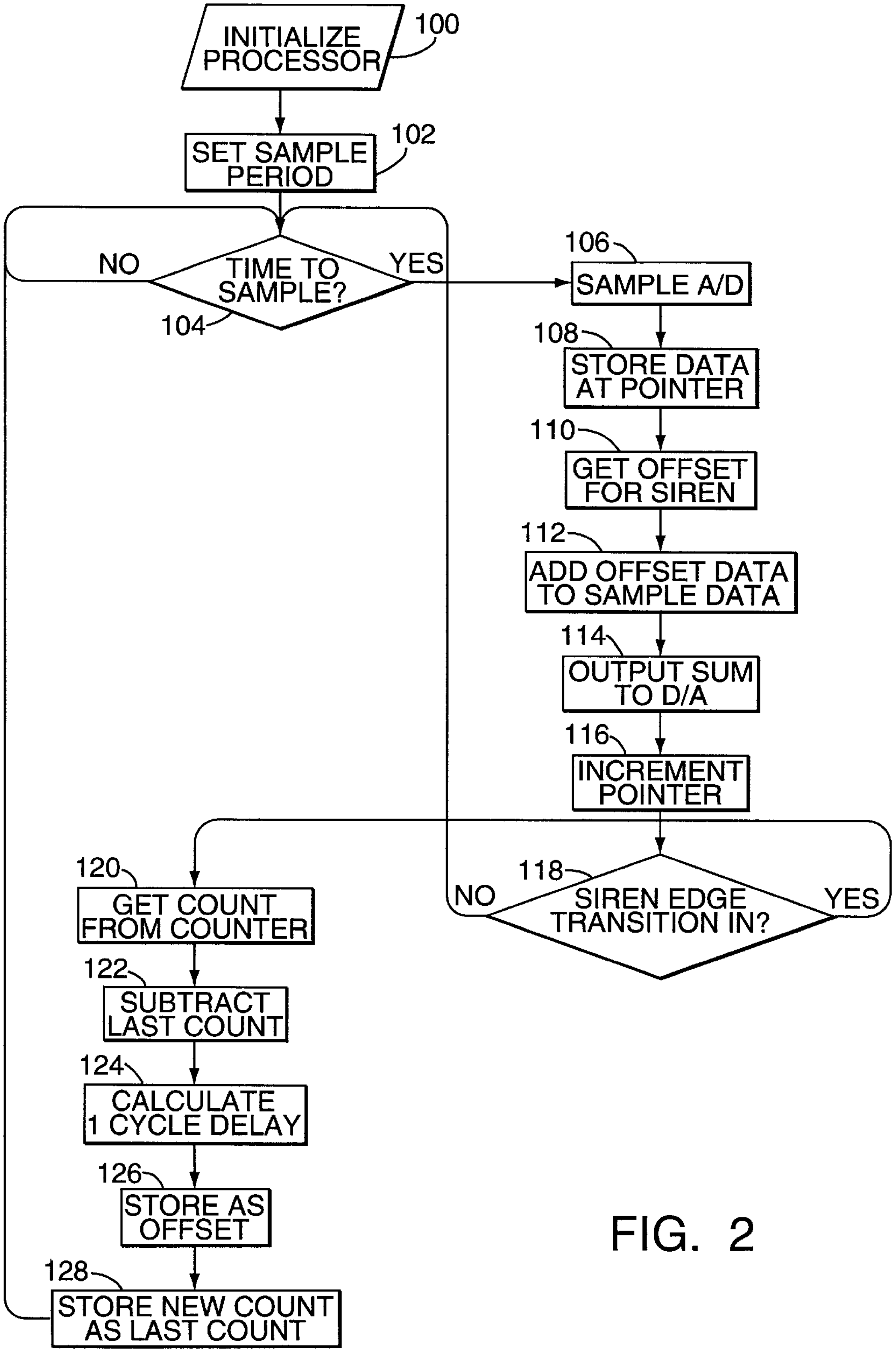
FIG. 2 is a flow chart of the procedural steps taken by the microprocessor of FIG. 1 for generating a processed information signal in which a noise component is negligible.

FIG. 2 illustrates in flow chart form an example of the procedural steps that may be taken by the microprocessor 22 of FIG. 1 for generating the processed information signal. The microprocessor 22 is initialized for operation (step 100). The predetermined period for sampling the information signal is then set (step 102). The desired sampling period corresponds to the selected characteristic frequency of the repetitive noise signal. For example, the sampling period may correspond to either a half period, full period, or multiple thereof of the repetitive noise signal, as was explained with respect to the operation of FIG. 1. The microprocessor 22 next determines if the sampling period can begin (step 104). If the previous sampling period has not yet finished (decision at step 104 is "No"), the microprocessor 22 waits until the previous sampling period has finished. Then the microprocessor 22 samples the digital information signal received from the A/D converter 14 (step 106). Each sample of the digital information is stored at a unique location in memory within the microprocessor 22 or in the external memory module 28 as referenced by a pointer (step 108). The microprocessor 22 next retrieves offset data associated with the delayed information signal which was sampled and delayed for a predetermined length of time corresponding to, for example, either a half or full period associated with the characteristic frequency of the noise signal (step 110). If the desired offset or delay time is a full period of the noise signal, the offset or delayed information signal is added to the currently sampled information signal to form the processed information signal. If the desired offset or delay is a half period of the noise signal, either the delayed information signal is subtracted from the currently sampled information signal, or the currently sampled information signal is subtracted from the delayed information signal to form the processed information signal (step 112). The digital processed information signal is then converted into analog form via the D/A converter (step 114) for transmission. The pointer corresponding to the current information signal sample is then incremented before the next sample is taken (step 116).

The microprocessor next determines if the noise signal has reached a transition edge of the noise signal indicating the end of a sample period (step 118). If the sample period has not ended, steps 106 through 116 are repeated. If the current sample period has ended, the microprocessor next retrieves the current pointer location (step 120). The pointer value at the end of the previous sample period is then subtracted from the current pointer value in order to determine the number of samples taken during the most recent sample period (step 122). A half or full noise signal period is then calculated as a function of the number of samples taken during the most recent sample period (124). The calculated period value is then stored in memory (step 126). The pointer value of the next to last sampling period is then replaced by the pointer value of the most recent sampling period for later use after the next sampling period is completed (step 128). The microprocessor next determines if a new sampling period should begin so as to repeat the sampling process (step 104).

Figure 3:
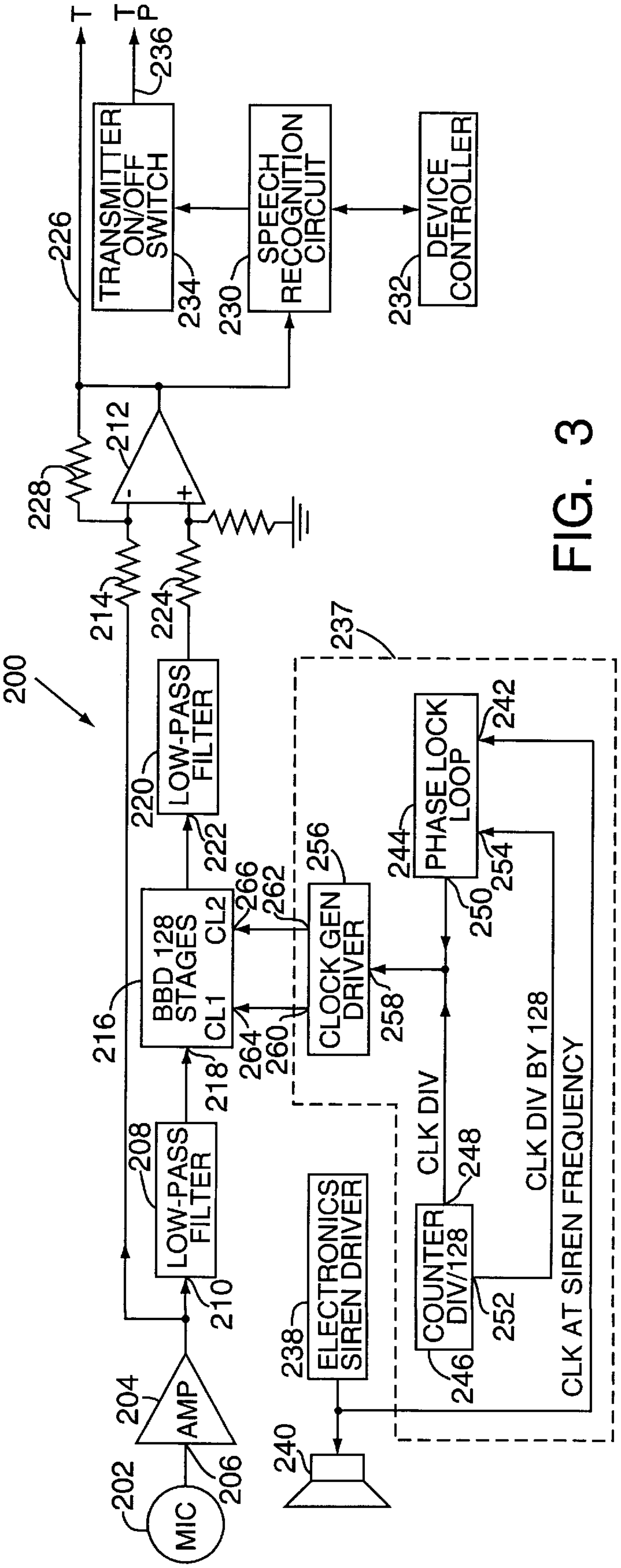
FIG. 3 schematically illustrates an analog embodiment of the microphone noise rejection system in accordance with the present invention.

FIG. 3 schematically illustrates an analog implementation of a noise rejection system 200 for substantially eliminating repetitive background noise from a microphone communication system. The noise rejection system 200 comprises an information signal interface, such as a microphone 202, for receiving an analog information or voice signal. The microphone 202 is coupled to an analog signal amplifier 204 at an input terminal 206. An output of the amplifier 204 is coupled to an input of a first low-pass filter 208 at 210, and to a negative input of a differential amplifier 212 via a resistor 214. An output of the first low-pass filter 208 is coupled to an input of a bucket brigade audio delay device (BBD) 216 at 218. As shown in FIG. 3, the BBD has 128 stages, and may, for example, be a charged coupled device (CCD) for transmitting the analog information. An output of the BBD 216 is coupled to an input of a second low-pass filter 220 at 222. An output of the second low-pass filter 220 is coupled to a positive input terminal of the differential amplifier 212 via a resistor 224.

An output of the differential amplifier 212 is coupled to a transmitter interface (not shown) along line 226 via a resistor 228. The output of the differential amplifier 212 is further coupled to a speech recognition circuit 230 that is coupled to a device controller 232, and to a transmitter on/off switch 234 for activating the transmitter interface via a control line 236.

The noise rejection system further includes an input interface 237 (shown within dashed lines) or means for identifying the characteristic frequency of one or more noise sources. The input interface may be embodied by any combination of standard components which cooperate to identify the characteristic frequency of a noise source. An example of an input interface 237 (as shown in the embodiment of FIG. 3) includes means for sensing the characteristic frequency when the characteristic frequency varies with time. As will be explained in more detail, the input interface 237 receives an analog signal from a siren driver 238 which drives a repetitive noise generator such as a siren or loudspeaker 240. Specifically, the input interface 237 includes a phase-locked loop (PLL) 244 having an internal voltage-controlled oscillator (VCO) and a first channel or reference frequency input 242 coupled to the siren driver 238. A free running counter/divide-by-128 circuit 246 has an input 248 coupled to an output 250 of the PLL 244 for receiving a voltage-controlled oscillator (VCO) clock signal generated by the PLL 244. The counter/divide circuit 246 in turn has an output 252 coupled to a second channel input 254 of the PLL 244 for transmitting a pulse signal to the PLL having a frequency 1/128 of the frequency of the VCO output of the PLL 244. In other words, for every 128 pulses the counter receives from the VCO clock output 250 of the PLL 244, the counter/divide circuit 246 sends a pulse to the second channel input 254 of the PLL 244. A comparator within the PLL compares the reference frequency of the noise signal received on the first channel 242 to the VCO/128 signal received on the second channel 254 for adjusting the bias of the VCO within the PLL 244 to generate a VCO clock signal at the output 250 of the PLL having a frequency that is 128 times the frequency of the noise signal.

A clock generator driver 256 has an input 258 coupled to the VCO clock output 250 of the phase-locked loop 244. The clock generator driver 256 further includes first and second control outputs 260, 262 coupled to respective first and second control inputs 264, 266 of the BBD 216.

The analog implementation of the noise rejection system 200 will now be explained in detail. The microphone 202 receives an information signal having an information component, such as a user's voice, and a repetitive noise component, such as a siren signal originating from the siren driver 238 and emanating from the loudspeaker 240. Simultaneous with the reception of the information signal, the siren driver 238 generates a repetitive noise signal which issues as a siren signal via the loudspeaker 240.

The noise signal having a varying characteristic frequency and associated period is sent to the first channel or reference signal input 242 of the PLL 244. The counter/divide circuit 246 sends a pulse to the second channel input 254 of the PLL 244 having an instant frequency equal to that of the VCO of the PLL divided by 128. The reference signal and the VCO/128 signal are then used by a comparator within the PLL 244 to adjust the frequency of the VCO output signal of the PLL 244 to be 128 times the instant frequency of the siren noise signal. The VCO clock signal is input to the clock generator driver 256 which in turn generates control signals at 260 and 262 for driving the BBD 216. During each period of the VCO clock signal, the clock generator driver sends control signals to the BBD at inputs 264, 266 informing the BBD to advance by one stage a portion of the analog signal stored therein. Because there are 128 stages in the BBD, and a portion of the information signal is stored in each stage 1/128 of the period of the noise signal, the information signal exiting the BBD has been delayed by a full period of the noise signal. The delayed information signal is then input to the positive input of the differential amplifier 212 to be added with a non-delayed or current information signal received by the differential amplifier 212 at its negative input. The non-delayed information signal is in effect subtracted from the delayed information signal to generate the processed information signal at the output of the amplifier 212. Alternatively, the delayed information signal may be subtracted from the non-delayed information signal in order to generate the processed information signal. The processed information signal may then be processed further by the device controller 232 and the speech recognition circuit 230 before being sent to the transmitter (not shown) that is activated by the transmitter on/off switch 234. Although the delay of the information signal has been described with reference to a full period of the noise signal, it may be desirable to delay the information a few full periods of the noise signal. Further, the delay may be an odd-numbered of half periods of the noise signal. In this case, the delayed and non-delayed information signals are added to one another in order to form the processed information signal.

Another embodiment of the input interface or identifying means may include a means for loading a predetermined clock frequency associated with the characteristic frequency (not shown) which is supplied to the BBD 216 when the characteristic frequency is at a constant and known value. Because the characteristic frequency is predetermined, there is no need for the PLL 244 and the counter/divide circuit 246 to sense the characteristic frequency in order to generate the clock frequency for driving the BBD 216.

While the present invention has been described in preferred embodiments, it will be understood that numerous modifications and substitutions can be made without departing from the spirit or scope of the invention. For example, the BBD of FIG. 3 may be employed to delay the information signal for an odd number of half periods or a few full periods of the noise signal in order to generate the processed information signal. The embodiment of FIG. 3 illustrates a mainly analog implementation of the noise rejection system, but a digital system relying primarily upon a microprocessor and software or a chip, as shown in FIGS. 1 and 2, may also be employed. As was previously mentioned, the invention also has broad application beyond emergency vehicle communication systems. For example, the noise rejection apparatus and method may be used in duplicated form in public address systems at sporting events and in other systems where horns, whistles or other repetitive noise generators, each having its own characteristic frequency or frequencies, are functioning simultaneously. The rejection apparatus can also be used for rejecting noise from information signals picked up by many other transducers in industrial, vehicular and other environments. Accordingly, the present invention has been described in preferred embodiments by way of illustration, rather than limitation.

What is claimed is:

1. A method of rejecting repetitive noise introduced into an information signal, comprising the steps of:

receiving from a first source a repetitive noise signal;

identifying a characteristic frequency of the repetitive noise signal received from the first source;

receiving from a second source that is distinct from the first source an information signal having an information component and a repetitive noise component originating from the first source;

delaying the information signal for a period of time based on the identified characteristic frequency of the repetitive noise signal to form a phase-shifted or delayed information signal; and processing the delayed information signal with a non-delayed information signal received from the second source to form a processed information signal in which the information component is substantial and the noise component is negligible.

2. A method as defined in claim 1, wherein the step of delaying comprises delaying the information signal by an odd number of half periods of the repetitive noise signal, and the step of processing comprises adding the delayed information signal to the non-delayed information signal to form the processed information signal.

3. A method as defined in claim 1, wherein the step of delaying comprises delaying the information signal by a half period of the repetitive noise signal, and the step of processing comprises adding the delayed information signal to the non-delayed information signal to form the processed information signal.

4. A method as defined in claim 1, wherein the step of delaying comprises delaying the information signal by one or more full periods of the repetitive noise signal, and the step of processing comprises subtracting the non-delayed information signal from the delayed information signal to form the processed information signal.

5. A method as defined in claim 1, wherein the step of delaying comprises delaying the information signal by one period of the repetitive noise signal, and the step of processing comprises subtracting the non-delayed information signal from the delayed information signal to form the processed information signal.

6. A method as defined in claim 1, wherein the first and second sources are respective microphone inputs.

7. A method as defined in claim 1, wherein the first source is a repetitive noise generator.

8. A method as defined in claim 1, wherein:

the step of delaying includes the steps of passing an analog information signal through an A/D converter to form a digital information signal, and delaying the digital information signal, and wherein:

the step of processing includes the steps of processing the delayed digital information signal with a non-delayed digital information signal to form a digital processed information, and passing the processed information signal through a D/A converter to form an analog processed information signal.

9. A method as defined in claim 8, wherein the step of delaying is accomplished by means of a microprocessor.

10. An apparatus for removing repetitive background noise from an information signal comprising:

a first input interface for receiving a repetitive noise signal and identifying a characteristic frequency of a repetitive noise signal from a repetitive noise generator;

a second input interface distinct from the first input interface for receiving an information signal having an information component and a repetitive noise component originating from the repetitive noise generator;

means for delaying the information signal for a period of time based on the characteristic frequency of the repetitive noise signal to form a phase-shifted or delayed information signal; and means for processing the delayed information signal with a non-delayed information signal received from the second input interface to form a processed information signal in which the information component is substantial and the noise component is negligible.

11. An apparatus as defined in claim 10, wherein the delaying means delays the information signal by an odd number of half periods of the repetitive noise signal, and the processing means adds the delayed information signal to the non-delayed information signal to form the processed information signal.

12. An apparatus as defined in claim 10, wherein the delaying means delays the information signal by a half period of the repetitive noise signal, and the processing means adds the delayed information signal to the non-delayed information signal to form the processed information signal.

13. An apparatus as defined in claim 10, wherein the delaying means delays the information signal by one or more full periods of the repetitive noise signal, and the processing means subtracts the non-delayed information signal from the delayed information signal to form the processed information signal.

14. An apparatus as defined in claim 10, wherein the delaying means delays the information signal by one period of the repetitive noise signal, and the processing means subtracts the non-delayed information signal from the delayed information signal to form the processed information signal.

15. An apparatus as defined in claim 10, wherein the delaying means includes a microprocessor.

16. An apparatus as defined in claim 10, wherein the first interface input is a repetitive noise generator and the second interface input is a microphone.

17. An apparatus as defined in claim 10, wherein the first interface input is a first microphone and the second interface input is a second microphone.

18. A method of rejecting repetitive noise from an information signal comprising the steps of:

receiving from a source an information signal containing a repetitive noise component;

identifying the period of the repetitive noise component;

delaying the information signal a length of time in accordance with the identified period of the repetitive noise component to produce a delayed information signal containing the repetitive noise component; and processing (1) a non-delayed information signal received from said source and containing the repetitive noise component and (2) the delayed information signal containing the repetitive noise component to produce a processed information signal from which the repetitive noise component is substantially eliminated.

19. A method as defined in claim 18, wherein the step of delaying comprises delaying the information signal by an odd number of half periods of the repetitive noise component, and the step of processing comprises adding the delayed information signal to the non-delayed information signal to form the processed information signal.

20. A method as defined in claim 18, wherein the step of delaying comprises delaying the information signal by one or more full periods of the repetitive noise component, and the step of processing comprises subtracting the non-delayed information signal from the delayed information signal to form the processed information signal.

21. An apparatus for removing repetitive background noise from an information signal comprising:

means for receiving from a source an information signal containing a repetitive noise component;

means for identifying the period of the repetitive noise component;

means for delaying the information signal a length of time in accordance with the identified period of the repetitive noise component to produce a delayed information signal containing the repetitive noise component; and means for processing (1) a non-delayed information signal received from said source and containing the repetitive noise component and (2) the delayed information signal containing the repetitive noise component to produce a processed information signal from which the repetitive noise component is substantially eliminated.

22. An apparatus as defined in claim 21, wherein the delaying means delays the information signal by an odd number of half periods of the repetitive noise component, and the processing means adds the delayed information signal to the non-delayed information signal to form the processed information signal.

23. An apparatus as defined in claim 21, wherein the delaying means delays the information signal by one or more full periods of the repetitive noise component, and the processing means subtracts the non-delayed information signal from the delayed information signal to form the processed information signal.

24. A method of rejecting repetitive noise introduced into an information signal, comprising the steps of:

identifying a characteristic frequency of a repetitive noise signal from a first source;

receiving from a second source that is distinct from the first source an information signal having an information component and a repetitive noise component originating from the first source;

delaying the information signal for a selected period of time based on the identified characteristic frequency of the repetitive noise signal to form a phase-shifted or delayed information signal;

processing the delayed information signal with the information signal which has not been delayed to form a processed information signal in which the information component is substantial and the noise component is negligible, and wherein the steps of identifying and delaying include:

generating a clock signal having a frequency that is a predetermined multiple of the characteristic frequency of the repetitive noise signal;

supplying the information signal to an input of a bucket brigade device having a predetermined number of stages between an input and output; and advancing portions of the information signal stage-by-stage through the bucket brigade device, the frequency of the clock signal determining the length of time each portion of the information signal remains in a stage, and the total time interval for a portion of the information signal to pass through the bucket brigade device corresponding to the desired delay for generating the delayed information signal.

25. A method as defined in claim 24, wherein the step of generating a clock signal includes employing a counter/divide circuit as a feedback loop in combination with a phase-locked loop circuit to multiply the characteristic frequency of the repetitive noise signal.

26. An apparatus for removing repetitive background noise from an information signal comprising:

a first input interface for identifying a characteristic frequency of a repetitive noise signal from a repetitive noise generator;

a second input interface distinct from the first input interface for receiving an information signal having an information component and a repetitive noise component originating from the generator;

means for delaying the information signal for a selected period of time based on the characteristic frequency of the repetitive noise signal to form a phase-shifted or delayed information signal, the delaying means including:

a phase-locked loop having first and second channel inputs and an output, the first input being connected with the first input interface for receiving the repetitive noise signal;

a counter/divide circuit having an input coupled to the output of the phase-locked loop and an output coupled to the second channel input of the phase-locked loop such that the phase-locked loop generates a clock signal at its output having a frequency that is a predetermined multiple of the characteristic frequency of the repetitive noise signal;

a clock driver having an input coupled to the output of the phase-locked loop for generating a control signal; and a bucket brigade device having a predetermined number of stages each storing portions of the information signal, the bucket brigade device including an input terminal for receiving the information signal, an output terminal for supplying a delayed information signal, and a control terminal for receiving the control signal from the phase-locked loop which instructs the bucket brigade device to advance a portion of the information signal by at least one stage, a total time interval for a portion of the information signal to pass through the bucket brigade device being equal to the desired delay to the information signal; and means for processing the delayed information signal with a non-delayed information signal to form a processed information signal in which the information component is substantial and the noise component is negligible.

* * * * *